United States Patent
Sandrin et al.

(10) Patent No.: US 11,439,367 B2
(45) Date of Patent: Sep. 13, 2022

(54) HYBRID ELASTOGRAPHY METHOD, PROBE AND DEVICE FOR HYBRID ELASTOGRAPHY

(71) Applicant: ECHOSENS, Paris (FR)

(72) Inventors: Laurent Sandrin, Bourg-la-Reine (FR); Hugo Bernard Martin Loree, Paris (FR)

(73) Assignee: ECHOSENS, Paris (FR)

(*) Notice: Subject to any disclaimer, the term of this patent is extended or adjusted under 35 U.S.C. 154(b) by 21 days.

(21) Appl. No.: 16/977,333

(22) PCT Filed: Feb. 26, 2019

(86) PCT No.: PCT/EP2019/054658
§ 371 (c)(1),
(2) Date: Sep. 1, 2020

(87) PCT Pub. No.: WO2019/166395
PCT Pub. Date: Sep. 6, 2019

(65) Prior Publication Data
US 2021/0052250 A1 Feb. 25, 2021

(30) Foreign Application Priority Data
Mar. 2, 2018 (FR) .................... 1851821

(51) Int. Cl.
*A61B 8/00* (2006.01)
*A61B 8/08* (2006.01)

(52) U.S. Cl.
CPC .............. *A61B 8/485* (2013.01); *A61B 8/085* (2013.01); *A61B 8/4444* (2013.01)

(58) Field of Classification Search
CPC ..... A61B 8/085; A61B 8/4416; A61B 8/4444; A61B 8/485; A61B 8/54
See application file for complete search history.

(56) References Cited

U.S. PATENT DOCUMENTS

2012/0271166 A1* 10/2012 Shao .................... G01N 29/348
600/438
2013/0024136 A1 1/2013 Gallippi et al.
(Continued)

FOREIGN PATENT DOCUMENTS

| EP | 2 739 211 A1 | 6/2014 |
| FR | 1351405 A | 2/1964 |
| WO | WO 2013/017532 A1 | 2/2013 |

OTHER PUBLICATIONS

Song, et al (Fast shear compounding using directional filtering and two-dimensional shear wave speed calculation, Proceeding of 2013 IEEE International Ultrasonics Symposium, pp. 1264-1267), 2013.*

(Continued)

*Primary Examiner* — Yi-Shan Yang
*Assistant Examiner* — Alexei Bykhovski
(74) *Attorney, Agent, or Firm* — Pillsbury Winthrop Shaw Pittman LLP (57) ABSTRACT

A hybrid elastography method includes application of a continuous low frequency vibration and generation, using an ultrasonic transducer in contact with the viscoelastic medium, of a first series of ultrasonic acquisitions, the first series of ultrasonic acquisitions including groups of ultrasonic acquisitions, the groups of ultrasonic acquisitions being generated with a first repetition rate, each group of ultrasonic acquisitions including at least one acquisition, the continuous vibration generating an elastic wave within the viscoelastic medium; application of a low frequency pulse and generation, using the ultrasonic transducer, of a second series of ultrasonic acquisitions, the ultrasonic acquisitions composing the second series being generated with a second repetition rate, the low frequency pulse generating a transient shear wave propagating within the viscoelastic medium; the continuous vibration applied by the first vibrator being stopped before the application of the low frequency pulse.

22 Claims, 7 Drawing Sheets

(56) References Cited

U.S. PATENT DOCUMENTS

| | | | |
|---|---|---|---|
| 2015/0374338 A1* | 12/2015 | Sandrin | A61B 8/485 |
| | | | 600/438 |
| 2016/0262706 A1* | 9/2016 | Zhao | A61B 5/7282 |
| 2018/0263595 A1* | 9/2018 | Goksel | A61B 8/085 |
| 2019/0041506 A1* | 2/2019 | Palmeri | G01S 15/8927 |
| 2019/0200951 A1* | 7/2019 | Meier | A61B 8/0841 |

OTHER PUBLICATIONS

Sandrin, L., et al, "Transient Elastography: A New Non-Invasive Method for Assessment of Hepatic Fibrosis," Ultrasound in Medicine and Biology, vol. 29, (2003), 1705-1713.

Nightingale, K., et al., "Acoustic Radiation Force Impulse Imaging: Ex-Vivo and In-Vivo Demonstration of Transient Shear Wave Propagation," IEEE Biomedical Imaging, (2002), pp. 525-528.

Bercoff, J., et al., "Supersonic Shear Imaging: A New Technique for Soft Tissue Elasticity Mapping," IEEE Transaction on Ultrasonics, Ferroelectrics, and Frequency Control, vol. 51, No. 4, (2004).

Muthupillai, R., et al., "Magnetic Resonance Elastography by Direct Visualization of Propagating Acoustic Strain Waves," Science, vol. 269, (1995), pp. 1854-1857.

Krouskop, T., et al., "A pulsed doppler ultrasonic system for making noninvasive measurements of the mechanical properties of soft tissues," Journal of Rehabilitation Research and Development, vol. 24, No. 2, (1987) pp. 1-8.

Tzschätzsch, H., et al., "In vivo time-harmonic multifrequency elastography of the human liver," Phys. Med. Biol., vol. 59, (2004), pp. 1641-1654.

International Search Report as issued in International Patent Application No. PCT/EP2019/054658, dated Apr. 16, 2019.

* cited by examiner

HYBRID ELASTOGRAPHY METHOD, PROBE AND DEVICE FOR HYBRID ELASTOGRAPHY

CROSS-REFERENCE TO RELATED APPLICATIONS

This application is the U.S. National Stage of PCT/EP2019/054658, filed Feb. 26, 2019, which in turn claims priority to French patent application number 1851821 filed Mar. 2, 2018. The content of these applications are incorporated herein by reference in their entireties.

TECHNICAL FIELD

The invention belongs to the field of elastography for determining the viscoelastic properties of a viscoelastic medium having an ultrasonic signal after ultrasonic illumination. The invention firstly relates to a hybrid elastography method including a harmonic elastography step and a transient elastography step. The invention secondly relates to a probe for the implementation of the hybrid elastography method. The invention thirdly relates to a hybrid elastography device. The hybrid elastography method according to the invention is particularly suited for determining the properties of a viscoelastic medium such as a human or animal liver.

PRIOR ART

Transient elastography (also called pulse elastography) is one of the best known and efficient methods for determining the elasticity of a viscoelastic medium. For example, transient elastography is commonly used to determine the elasticity of the liver in humans or animals.

In transient elastography a pulse shear wave is generated and its propagation velocity within the viscoelastic medium of interest is measured. The propagation velocity of the shear wave next makes it possible to compute the Young's modulus of the medium and thus to measure its elasticity.

Several techniques exist for implementing transient elastography.

For example, the Applicant has developed and commercialised a vibration controlled transient elastography (VCTE) technique. The device implementing this technique, called Fibroscan®, is capable of measuring the elasticity of the human liver in a rapid, non-invasive and reproducible manner. In such a transient elastography device, the shear wave is generated by a vibrator placed in contact with the medium to characterise. The propagation of the shear wave is next monitored using a series of ultrasonic acquisitions realised by an ultrasonic transducer with high repetition rate. Each ultrasonic acquisition corresponds to at least one ultrasonic emission. Each ultrasonic emission may be associated with the detection and the recording on the go of the echoes generated by the reflective particles present in the studied medium for a defined range of depths. The reflected ultrasonic signals are processed by correlation to work back to the movements of the tissue generated by the propagation of the shear wave as a function of time and the position in the medium. The study of these movements makes it possible to work back to the propagation velocity of the shear wave within the viscoelastic medium, and thus to the elasticity of the tissues, as is explained in the document "Transient Elastography: a new non-invasive method for assessment of hepatic fibrosis" of L. Sandrin et al., published in Ultrasound in Medicine and Biology, Vol. 29, pages 1705-1713, 2003.

The VCTE technique is particularly advantageous because it makes it possible to separate in time the propagation of the shear wave and the propagation of the compression waves generated at the same time as the shear wave, the two types of waves having very different propagation velocities. The compression wave propagates at around 1500 m/s, it may be considered as infinitely rapid compared to the shear wave of which the propagation velocity is typically comprised between 1 and 10 m/s. Indeed, such a separation is important because the presence of compression waves at the same time as the shear wave introduces a systematic error into the measurement of the propagation velocity of the shear wave.

One of the main limitations of the VCTE technique is the difficulty of validating the positioning of the probe before carrying out the elasticity measurement and thus the triggering of a mechanical pulse. Indeed an incorrect positioning of the probe may result in an imperfect propagation of the shear wave or even the absence of shear wave. For example, the propagation of the shear wave may be perturbed by the presence of rebounds linked to the proximity of edges of the studied organ or not propagate at all in the presence of a liquid interface between the probe and the studied medium. It is in fact known that shear waves do not surmount liquid barriers; this is in particular the case in the presence of ascites in the abdomen. The measurement of the resulting elasticity would thus be invalid.

Today it is possible to use ultrasounds to guide the positioning of the vibrator for transient elastography. For example, it is possible to use ultrasonic imaging or a targeting tool such as that described in the patent application EP2739211 A1. However, these solutions are not satisfactory because they do not make it possible to predict directly an incorrect propagation of the shear wave linked for example to an incorrect positioning of the probe or to the presence of a liquid interface.

Among the other transient elastography techniques, it is possible to cite those based on the generation of a shear wave by radiation force or "Acoustic Radiation Force Impulse"—ARFI. This technique is for example described in the document "Acoustic Radiation Force Impulse Imaging: Ex-vivo and in-vivo demonstration of transient shear wave propagation" of K. Nightingale et al. published in IEEE Biomedical Imaging, 2002.

Another transient elastography technique is described in the document "Supersonic Shear Imaging: A new technique for soft tissue elasticity mapping" of J. Bercoff et al., published in IEEE Transactions on Utrasonics, Ferroelectrics, and Frequency Control, 2004. According to this technique, the shear waves are generated by radiation force by focusing an ultrasonic beam at different points in the medium, which makes it possible to obtain shear waves having a flat wave front.

However, none of these transient elastography techniques provides a simple and complete solution to the problem of positioning the probe in order to obtain a measurement of elasticity that is valid in a certain manner.

So-called harmonic elastography techniques also exist. These techniques are based on the application of a continuous vibration having a frequency comprised between 30 Hz and 100 Hz. The elastic waves created within the medium are quasi-stationary waves, superimpositions of shear waves and compression waves.

Among existing harmonic elastography techniques, it is possible to cite:

- The so-called "Magnetic Resonance Elastography" or MRE technique in which magnetic resonance imaging is used to view the quasi-stationary waves generated in the medium; this technique is described in the document "Magnetic resonance elastography by direct visualization of propagating acoustic strain waves" of R. Muthupillai et al., published in Science 269, 1995. This technique is guided by MRI;
- The so-called Sono Elastography technique described for example in the document "A pulsed doppler ultrasonic system for making noninvasive measurements of the mechanical properties of soft tissues" of T. Krouskop, published in Journal of Rehabilitation Research and Development, 24, 1987. This technique is guided by echographic imaging;
- The so-called "Time Harmonic Elastography" technique described for example in the document "In vivo time-harmonic multifrequency elastography of the human liver" of H. Tzschatzsch et al., published in Phys. Med. Biol., 59, 2004. This technique is guided by echographic imaging.

Even if these techniques do not require creating a pulse shear wave which propagates in the medium to characterise, they have certain difficulties.

For example, in harmonic elastography, it is impossible to separate the shear waves and the compression waves which are created at the same time in the medium to characterise. The quasi-stationary elastic wave created within the medium to characterise is thus a superimposition of quasi-stationary shear and compression waves. Since the velocity of the shear waves is much lower than the velocity of the compression waves, the velocity of the vibration really observed does not correspond to the velocity of a shear wave. It is thus necessary to take into account the effect of the propagation of the compression waves before being able to measure the propagation velocity of the shear waves. To do so, it is necessary to record complex data and to compute displacements in the three directions of space x, y, z.

The only harmonic elastography technique presently capable of carrying out such a correction is the MRE technique. However, this technique requires a magnetic resonance imaging device, very complex and expensive, and thus much more difficult to implement than the VCTE technique.

Furthermore, these techniques are guided by traditional methods of echographic imaging or magnetic resonance imaging type. They thus require considerable expertise of the operator, which is not favourable to widespread dissemination of the technology.

Furthermore, the harmonic elastography technique may be used to guide treatment methods. It involves for example treating tumours located by the harmonic elastography technique by means of hyperthermia type methods.

Technical Problem

Harmonic or transient elastography techniques rely on a guiding of the measurement using a traditional imaging technique (echographic imaging or magnetic resonance imaging) which requires considerable expertise of the operator and does not ensure optimal localisation of the tissue to characterise as regards the propagation of the shear waves. The result is the impossibility of predicting the validity of the elastography measurement that is going to be carried out.

Finally, these techniques are not suited to an implementation with devices of small size and that are easy to use.

SUMMARY OF THE INVENTION

To resolve at least partially these problems, the present invention describes a novel elastography technique which will be called in the remainder of this document hybrid elastography.

To this end the invention firstly relates to a hybrid elastography method including the following steps:
- application, using a first vibrator comprised in a probe in contact with a viscoelastic medium, of a continuous low frequency vibration and generation, using an ultrasonic transducer in contact with the viscoelastic medium, of a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition, the continuous vibration generating an elastic wave within the viscoelastic medium;
- application, using a second vibrator comprised in the probe in contact with a viscoelastic medium, of a low frequency pulse and generation, using the ultrasonic transducer, of a second series of ultrasonic acquisitions, the ultrasonic acquisitions composing the second series being generated with a second repetition rate, the low frequency pulse generating a transient shear wave propagating within the viscoelastic medium.

According to one embodiment, the continuous vibration applied by the first vibrator is stopped before the application of the low frequency pulse by the second vibrator and the generation of the second series of ultrasonic acquisitions.

Hybrid elastography is taken to mean a method for implementing an elastography technique including at least one step of application of a continuous low frequency vibration and a step of application of a low frequency pulse. In other words, the hybrid elastography method according to the invention includes both a generation of a continuous vibration, which is characteristic of a harmonic elastography technique, and a generation of a low frequency pulse, which is characteristic of a transient elastography technique.

Thus the continuous low frequency vibration which is continuous and the low frequency pulse of which the duration is brief are distinguished. Typically the duration of the low frequency pulse is comprised between $\frac{1}{2}*tSWF$ and $20/tSWF$, tSWF being the central frequency of the low frequency pulse.

Continuous low frequency vibration is taken to mean continuous reproduction of a wave form pattern. This pattern may for example be a perfect sinusoid; this is then known as monochromatic vibration. The vibration may also be constituted by the reproduction of an arbitrary pattern. According to one embodiment, the continuous vibration is interrupted during switching to low frequency pulse mode, to stop the measurement process or when the measurement conditions are no longer satisfactory. The measurement conditions being able to be for example a condition on the contact force with the studied medium. The central frequency of the continuous low frequency vibration is typically comprised between 5 and 500 Hz.

Elastic wave is taken to mean the superimposition of compression waves and shear waves.

Ultrasonic acquisition is taken to mean the emission of an ultrasonic shot. Said ultrasonic emission may be associated with the detection and the recording on the go of the echoes generated by the reflective particles present in the studied medium for a defined range of depths.

The first series of ultrasonic acquisitions is thus formed by a repetition of groups of acquisitions. A group of acquisitions includes at least one ultrasonic acquisition. The groups of acquisition are emitted or generated with a first repetition rate. The first repetition rate is also called inter-group repetition rate. The first repetition rate is typically comprised between 5 and 500 Hz.

When each group of acquisitions is formed by at least two ultrasonic acquisitions, the ultrasonic acquisitions forming a same group are emitted or generated with an intra-group repetition rate typically comprised between 500 Hz and 100 kHz.

Advantageously, the use of a first low repetition rate during the application of the continuous vibration makes it possible to measure the movements of the viscoelastic tissue while limiting the acoustic energy sent into the same tissue so as not to exceed the peak and average acoustic power limits.

The term displacement is considered in the wider sense in this document. It encompasses any movement parameter such as the displacement, the velocity, the deformation, the deformation rate, the velocity of deformation and any mathematical transformation applied to these parameters.

Low frequency pulse is taken to mean a pulse of which the central frequency is typically comprised between 5 and 500 Hz.

Second series of ultrasonic acquisitions is taken to mean a series of ultrasonic acquisitions emitted or generated with a repetition rate greater than 500 Hz and preferably comprised between 500 Hz and 100 kHz.

During the application of the continuous vibration, an elastic wave is generated within the viscoelastic medium.

The first series of ultrasonic acquisitions is used to study the propagation of the elastic wave within the viscoelastic medium. It is possible to detect the echoes or ultrasonic signals reflected by the viscoelastic medium and to compute, from these reflected ultrasonic signals, the displacements of the viscoelastic medium caused by the propagation of the elastic wave within the viscoelastic medium generated by the continuous vibration.

For example, it is possible to compute the displacements of the viscoelastic medium by applying a correlation technique to the ultrasonic acquisitions composing a same group of acquisitions of the first series of ultrasonic acquisitions.

It is then possible to measure the properties of the elastic wave within the medium and to compute in real time a positioning indicator from the measured properties. This indicator is displayed in real time to guide the operator. Examples of such properties are the amplitude and the phase of the elastic wave, measured as a function of the depth in the tissue to characterise. It is also possible to compute the phase velocity of the elastic wave. However, an elasticity value may be deduced from the phase velocity of the elastic wave but the latter differs from the elasticity value deduced with the pulse wave given the superimposition of shear waves and compression waves during the application of the continuous vibration.

In the remainder of this document "positioning indicator" and "real time positioning indicator" refer to the same real time positioning indicator.

Real time is taken to mean an indicator of which the display is regularly refreshed during the examination. In general, the refresh rate is around 20 Hz but may also be of the order of 1 Hz.

It is important to note that the continuous vibration is used to verify the positioning of the probe used for the hybrid elastography. As an example, the continuous vibration may be used to verify the presence of the hepatic parenchyma facing the probe. It is important to note that the continuous vibration is not used to replace the measurement carried out with the pulse; it completes this measurement. In other words, during the step of application of a continuous vibration, the indirect measurement of the viscoelastic properties of the medium is possible but not indispensable. This latter measurement is not physically identical to the elasticity in the sense of the Young's modulus but may be correlated with this value.

The application of a low frequency pulse generates a transient shear wave propagating within the viscoelastic medium to characterise. The monitoring of the propagation of the shear wave makes it possible to measure the viscoelastic properties of the tissue to characterise, for example the propagation velocity of the shear wave, the elasticity of the tissue, the shear modulus of the tissue or the Young's modulus of the tissue. Thanks to the method according to the invention, the measurement of the viscoelastic properties of the medium may be disregarded if the positioning of the probe is not satisfactory. In other words, it is possible to validate a priori the measurement of elasticity by using a positioning indicator obtained during the step of application of a continuous vibration.

Alternatively, the application of the low frequency pulse may be only triggered if the positioning of the probe has been validated beforehand during the harmonic elastography step.

The second series of ultrasonic acquisitions emitted or generated with a second repetition rate is used to study the propagation of the transient shear wave within the viscoelastic medium to characterise. It is possible to record the ultrasonic signals reflected by the viscoelastic medium and to compute from these reflected ultrasonic signals the displacements of the viscoelastic medium caused by the propagation of the shear wave. The measurement of the displacements generated in the viscoelastic medium by said propagation next makes it possible to work back to the propagation velocity of the shear wave and thus to the elasticity of the medium using the formula $E=3\rho V_s^2$ where E is the elasticity or Young's modulus, $\rho$ the density and $V_s$ the shear velocity.

The hybrid elastography method according to the invention thus makes it possible to validate the positioning of the probe using a harmonic elastography technique and next to measure the viscoelastic properties of the medium to characterise by using a transient or pulse elastography technique. In particular, once the positioning of the probe has been validated, a measurement of the viscoelastic properties is carried out during the transient elastography step. This measurement provides a more precise value of the viscoelastic properties of the medium than with harmonic elastography because in pulse elastography the compression and shear waves are not superimposed, unlike what is observed in harmonic elastography.

In other words, the first step of harmonic elastography makes it possible to guide the positioning of the probe with regard to the tissue to characterise by providing to the operator an indicator predictive of the success of the measurement by pulse elastography. Once the positioning of the probe has been validated, it is possible to trigger an acquisition in transient elastography, the transient shear wave propagating correctly within the medium.

Advantageously, the hybrid elastography method according to the invention makes it possible to carry out a measurement of the viscoelastic properties of the tissue to characterise in a reliable and reproducible manner using a transient elastography technique, while positioning the probe in a simple and precise manner thanks to a harmonic elastography technique.

The hybrid elastography method according to the invention may also have one or more of the characteristics below, considered individually or according to all technically possible combinations thereof:

- The hybrid elastography method according to the invention further includes the following steps:
    - determination, from the first series of ultrasonic acquisitions, of at least one property of the elastic wave within the viscoelastic medium;
    - determination, from the second series of ultrasonic acquisitions, of at least one property of the transient shear wave and a property of the viscoelastic medium;
- the same vibrator is used to apply the continuous low frequency vibration and the low frequency pulse;
- a property of the elastic wave within the viscoelastic medium is used to compute a real time positioning indicator of the probe with respect to the viscoelastic medium to study;
- the method according to the invention further includes a step of displaying in real time the real time positioning indicator; the refresh rate of the display is for example greater than or equal to 5 Hz;
- the step of computation and the step of displaying the positioning indicator and its display are carried out concomitantly.
- the step of application of the low frequency pulse and generation of the second series of ultrasonic acquisitions is only triggered if the real time positioning indicator satisfies a predetermined condition;
- the step of application of the low frequency pulse and generation of the second series of ultrasonic acquisitions is triggered automatically on the basis of the value of the real time positioning indicator;
- the step of application of the low frequency pulse and generation of the second series of ultrasonic acquisitions is triggered automatically;
- the step of application of the continuous low frequency vibration is only triggered if the contact force between the vibrator and the viscoelastic medium is above a predetermined lower threshold;
- the step of application of the continuous low frequency vibration is only triggered if the contact force between the vibrator and the viscoelastic medium is comprised between a predetermined lower threshold and a predetermined upper threshold;
- the step of application of a low frequency pulse is only triggered if the contact force between the vibrator and the viscoelastic medium is above a predetermined lower threshold;
- the upper and lower contact force thresholds for the application of the continuous vibration are typically equal to respectively 1 N and 10 N;
- the upper and lower contact force thresholds for the application of the low frequency pulse are typically equal to respectively 4 N and 10 N;
- the frequency of the continuous low frequency vibration, cSWF, applied by the vibrator is comprised between 5 and 500 Hz;
- the amplitude of the continuous low frequency vibration applied by the vibrator is comprised between 10 μm and 5 mm;
- the first series of ultrasonic acquisitions is formed by a repetition of groups including at least two ultrasonic acquisitions having an intra-group repetition rate comprised between 500 Hz and 10 kHz and a first repetition rate comprised between 10 Hz and 10 kHz;
- the first repetition rate is lower than the continuous vibration frequency;
- the central frequency tSWF of the low frequency pulse is comprised between 10 Hz and 1000 Hz;
- the pulse duration is comprised between $1/(2*tSWF)$ and $20/tSWF$, tSWF being the central frequency of the low frequency pulse;
- the repetition rate of the second series of ultrasonic shots is comprised between 500 Hz and 100 kHz;
- the amplitude of the low frequency pulse is comprised between 100 μm and 10 mm;
- the stopping of the continuous vibration of the vibrator and the application of the low frequency pulse are separated by a time interval, the time interval being able to be greater than or equal to 10 ms and preferably being comprised between 1 ms and 50 ms;
- the amplitude of the low frequency pulse is determined on the basis of the properties of the elastic wave created by the continuous vibration.

The present invention also relates to a probe for the implementation of the hybrid elastography method according to the invention. The probe according to the invention includes:

- A first vibrator configured to apply to the viscoelastic medium a continuous low frequency vibration, the continuous low frequency vibration generating an elastic wave within the viscoelastic medium;
- A second vibrator configured to apply to the viscoelastic medium a low frequency pulse generating a transient shear wave within the viscoelastic medium;
- An ultrasonic transducer configured to emit:
    - a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition;
    - a second series of ultrasonic acquisitions, the ultrasonic acquisitions composing the second series being generated with a second repetition rate;

said probe being further configured to stop the application of the continuous vibration before the application of the low frequency pulse.

The probe according to the invention enables the implementation of the method according to the invention.

According to one embodiment, the probe according to the invention includes a single vibrator that is used both to apply a continuous vibration to the viscoelastic medium during the harmonic elastography step and to apply a low frequency pulse during the pulse elastography step.

The probe is configured so that the application of the low frequency pulse and the stopping of the continuous vibration are separated by a time interval comprised between 1 ms and 50 ms. Preferably the time interval is greater than or equal to 10 ms.

The ultrasonic transducer is used to send the first and the second series of ultrasonic acquisitions within the viscoelastic medium. The same ultrasonic transducer detects the reflected ultrasonic signals at each acquisition. The reflected ultrasonic signals are next processed to detect the displacements of the viscoelastic medium caused by the continuous low frequency vibration and the low frequency pulse.

The probe for hybrid elastography according to the invention may also have one or more of the characteristics below, considered individually or according to all technically possible combinations thereof:
- the vibrator is an electric motor or an audio reel or an electrodynamic actuator;
- the ultrasonic transducer is mounted on the axis of a vibrator;
- the hybrid elastography probe according to the invention further includes means for triggering the application of a low frequency pulse;
- the ultrasonic transducer is circular with a diameter comprised between 2 mm and 15 mm;
- the ultrasonic transducer has an operating frequency comprised between 1 MHz and 15 MHz;
- the ultrasonic transducer is a convex abdominal probe;
- the first and second vibrators are axisymmetric;
- at least one of the two vibrators is axisymmetric;
- at least one vibrator has the same axis of symmetry as the ultrasonic transducer;
- at least one vibrator has a ring shape and is arranged around the ultrasonic transducer;
- the probe further includes means for computing and displaying the real time positioning indicator.

The present invention also relates to a hybrid elastography device implementing the hybrid elastography method according to the invention.

Such a hybrid device according to the invention includes:
A hybrid elastography probe according to the invention;
A central unit connected to the probe and including at least computing means for processing the reflected ultrasonic signals, display means and control and/or input means.

According to one embodiment, the display means are used to display in real time the real time positioning indicator.

LIST OF FIGURES

Other characteristics and advantages of the invention will become clear from the description that is given thereof below, for indicative purposes and in no way limiting, with reference to the appended figures among which.

DETAILED DESCRIPTION

Figure 1:
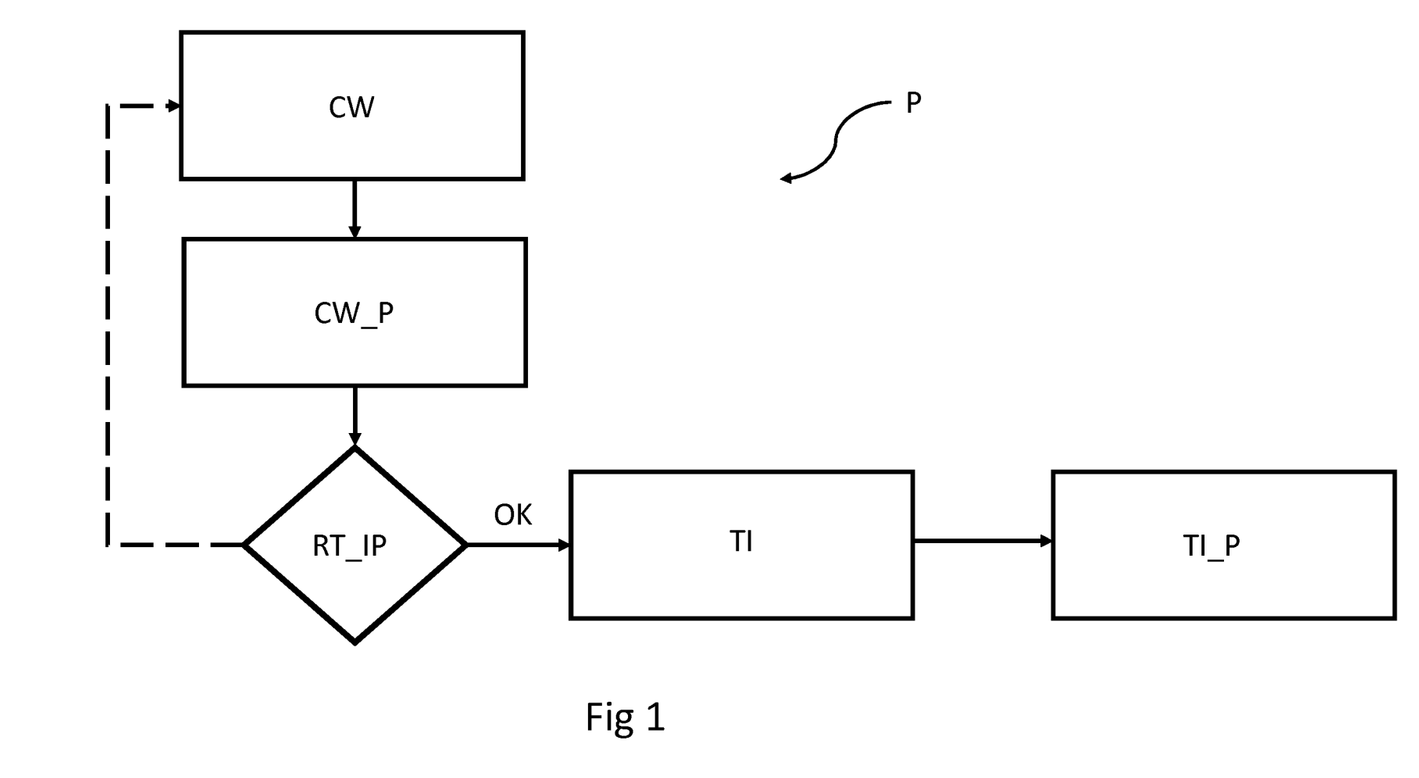
FIG. 1 illustrates the steps of the hybrid elastography method according to the invention.

FIG. 1 illustrates the steps of the hybrid elastography method P according to the invention.

The first step CW of the method P includes the application of a continuous low frequency vibration using a first vibrator comprised in a probe in contact with the viscoelastic medium.

The frequency of the continuous vibration is comprised between 5 and 500 Hz.

The first step CW of the method P also includes the generation, by the ultrasonic transducer, of a first series of ultrasonic acquisitions. The first series of ultrasonic acquisitions includes groups of ultrasonic acquisitions. The groups of ultrasonic acquisitions are emitted with a first repetition rate LPRF comprised between 5 Hz and 500 Hz, each group including at least one ultrasonic acquisition.

An ultrasonic acquisition includes the emission of an ultrasonic shot followed by the detection and the recording of the reflected ultrasonic signals or echoes.

The application of a continuous vibration to the viscoelastic medium generates an elastic wave within the same medium. The elastic wave is formed by a superimposition of shear waves and compression waves. The study of the properties of this elastic wave makes it possible to obtain information concerning the correct positioning of the probe with regard to the viscoelastic medium.

The viscoelastic medium to characterise diffuses at least partially the ultrasonic shots. It is thus possible to detect the ultrasonic signals reflected during the emission of the first series of ultrasonic acquisitions.

The detection of the reflected ultrasonic signals may be carried out using the same ultrasonic transducer used for the emission.

The reflected ultrasonic signals detected during the step of generation of a first series of ultrasonic acquisitions CW are processed during a step of determining at least one property of the elastic wave within the viscoelastic medium CW_P.

During this step, the reflected ultrasonic signals are correlated with each other so as to measure the displacements of the viscoelastic medium caused by the elastic wave generated by the application of the continuous vibration, according to a technique known in the field of elastography and more generally ultrasounds.

From the displacements measured within the viscoelastic medium, it is possible to compute properties of the elastic wave such as the amplitude and the phase as a function of the position within the viscoelastic medium. The position of a point within the viscoelastic medium is measured as the distance between the ultrasonic transducer and said point computed along the direction of propagation of the ultrasounds emitted by the transducer. For this reason the position of a point within the viscoelastic medium is generally called depth.

It is also possible to determine other parameters of the elastic wave within the viscoelastic medium, such as the phase velocity of the elastic wave.

The variations in the amplitude and the phase of the elastic wave as a function of depth within the tissue may be computed. By carrying out an adjustment between the theoretical model and the measured properties, it is possible to extract an adjustment quality parameter. From this adjustment quality parameter and/or other properties of the elastic wave, it is possible to compute a real time positioning indicator RT_IP of the vibrator with respect to the tissue to characterise.

Thanks to the use of a low first repetition rate LPRF for the first series of ultrasonic acquisitions, it is possible to compute the real time positioning indicator RT_IP in real time.

According to one embodiment, the real time positioning indicator RT_IP is displayed concomitantly with its computation. In other words, the real time positioning indicator is computed and displayed in real time. In other words the step of computation of the real time positioning indicator and the step of displaying the real time positioning indicator are carried out concomitantly.

For example, one of the theoretical models used provides a linear variation of the phase lag at the central frequency of the elastic wave with depth in the medium to characterise. In this case the adjustment is a linear adjustment and the adjustment quality parameter translates the linearity of the phase as a function of depth in the medium. A possible indicator is the determination coefficient $R^2$ giving the quality of the prediction of the linear regression of the curve of the phase lag as a function of depth in the studied depth range.

According to one embodiment the step CW_P of determining at least one property of the elastic wave within the tissue is carried out at the same time as the step of applying the continuous vibration CW and detecting the first reflected ultrasonic signals.

Thanks to the method P according to the invention it is thus possible to measure in real time the properties of the elastic wave within the tissue and to obtain in real time the real time positioning indicator RT_IP of the probe.

Advantageously, a low first repetition rate LPRF makes it possible to reduce the size of the data recorded during the step of generating the first series of ultrasonic acquisitions CW and to process these data in real time to obtain the positioning indicator RT_IP.

If the value of the positioning indicator is not satisfactory, the two steps CW and CW_P are repeated as is illustrated by the dashed arrow in FIG. 1.

If the value of the positioning indicator is satisfactory, the probe is correctly positioned with regard to the viscoelastic medium and the measurement of elasticity carried out during the transient elastography step will be valid. In this case the method P according to the invention provides the passage to step TI.

According to one embodiment, the method P according to the invention includes a step of displaying in real time the positioning indicator RT_IP. The computation of the positioning indicator RT_IP and its display are carried out concomitantly.

According to one embodiment, the refresh rate of the display of the positioning indicator is greater than or equal to 5 Hz.

The step TI illustrated in FIG. 1 includes the application of a low frequency pulse using a second vibrator.

As in any transient elastography technique, the application of a low frequency pulse to the viscoelastic medium generates a transient or pulse shear wave propagating within the medium. By measuring the propagation velocity of the transient shear wave within the medium to characterise it is possible to work back to the elasticity of the medium.

It is important to note that during the application of the low frequency pulse and the following steps, the continuous low frequency vibration is stopped. The stopping of the continuous vibration during the implementation of the transient elastography step is very important to enable the temporal separation of the compression waves and the shear waves, which makes it possible to obtain a reliable measurement of the elasticity of the medium.

According to one embodiment, between the stopping of the continuous vibration and the application of the low frequency pulse there is a time interval comprised between 1 ms and 50 ms and preferably greater than or equal to 10 ms. This time interval enables the dissipation of the compression waves generated by the continuous vibration and improves the precision and the reliability of the measurement of a viscoelastic property such as the velocity of the transient shear wave.

At the same time as the application of the low frequency pulse, the step TI includes the generation, using the ultrasonic transducer, of a second series of ultrasonic acquisitions emitted with a second repetition rate VHPRF.

The repetition rate VHPRF of the second series of ultrasonic acquisitions is comprised between 500 Hz and 100 kHz.

From the reflected ultrasonic signals detected during the step TI, it is possible to compute at least one property of the viscoelastic medium during a step Ti_P of the method P according to the invention. This is possible by applying correlation techniques well known in elastography. In particular, as is explained for example in the document "Transient Elastography: a new non-invasive method for assessment of hepatic fibrosis" of L. Sandrin et al., it is possible to compute the propagation velocity of the shear wave and thus the elasticity of the viscoelastic medium.

For example, during the step TI_P of determining a property of the viscoelastic medium, the propagation velocity of the pulse shear wave generated by the low frequency pulse is determined. From the propagation velocity of the shear wave it is possible to work back to the elasticity, the shear modulus or the Young's modulus of the viscoelastic medium.

According to one embodiment, the steps of applying a low frequency pulse and generating the second series of ultrasonic acquisitions are only triggered if the positioning indicator satisfies a predetermined condition.

Advantageously, this makes it possible to trigger only valid measurements of elasticity, because the existence of the transient shear wave and its correct propagation are ensured by the positioning indicator.

The triggering of the steps of applying a low frequency pulse and following steps may be automatic or manual and activated for example by the operator on the basis of the value of the positioning indicator RT_IP.

If the application of a low frequency pulse is triggered by the operator, the positioning indicator computed in real time during the step CW_P is displayed in real time.

According to one embodiment, a simpler signal of "Positioning OK" or "Positioning NOT OK" type may be displayed to communicate with an operator.

According to one embodiment, the refresh rate of the display of the positioning indicator is greater than 5 Hz.

This allows the operator to trigger the elasticity measurement from the moment that a correct propagation of the shear wave is observed ensuring the validity of the measurement.

According to one embodiment, the continuous vibration is only triggered if the contact force between the vibrator and the viscoelastic tissue is above a predetermined threshold, which is typically 1 N.

According to one embodiment, the continuous vibration is only triggered if the contact force between the vibrator and the viscoelastic tissue is below a predetermined threshold, which is typically 10 N.

Advantageously, the lower threshold ensures a sufficient coupling between the probe and the viscoelastic medium and the upper threshold avoids deforming the continuous vibration caused by an excessive contact force and damaging the studied medium.

According to one embodiment, the low frequency pulse is only triggered if the contact force between the vibrator and the viscoelastic tissue is comprised between a predetermined lower threshold and a predetermined upper threshold.

The two thresholds are typically respectively 4 N and 8 N.

Advantageously, the lower threshold ensures sufficient coupling between the probe and the viscoelastic medium and the upper threshold avoids deforming the low frequency pulse caused by excessive contact force and damaging the studied medium.

On account of the continuous vibratory movement of the vibrator, the determination of the contact force between the vibrator and the medium is more complex than in the case of a standard transient elastography method. In the presence of the continuous low frequency vibration, the contact force between the vibrator and the viscoelastic medium is given by the following formula:

$$F=k(x+A\times\cos(2\pi f_{low}t))$$

In this formula x is the displacement of the vibrator, k the elastic constant of the spring placed in the probe, A the amplitude of the continuous vibration and $f_{low}$ the continuous vibration frequency.

The force F may be measured using a force sensor placed on the hybrid elastography probe. Successively by applying a low pass filter to the signal thereby measured, it is possible to eliminate the low frequency part and to deduce the average contact force:

$$F_{Average}=k(x)$$

According to one embodiment of the method P according to the invention, the low frequency pulse is only triggered if the value of $F_{Average}$ is above a predetermined threshold.

Advantageously, the use of a minimal contact force value makes it possible to ensure a good transmission of the low frequency pulse to the viscoelastic medium and a correct propagation of the transient shear wave generated within the medium.

According to one embodiment of the method P according to the invention, the stopping of the continuous vibration of the vibrator and the application of the low frequency pulse are separated by a time interval comprised between 1 ms and 50 ms. Preferably, the time interval is greater than or equal to 10 ms.

Advantageously, the use of a time interval separating the stopping of the continuous vibration and the application of a low frequency pulse enables the dampening of the vibration generated by the continuous vibration. It is thus possible to apply the low frequency pulse and to observe the propagation of the pulse shear wave in the absence of the elastic wave. The concomitant presence of the elastic wave including the compression wave and the transient shear wave could introduce an error into the measurement of the propagation velocity of the transient shear wave.

Figure 2:
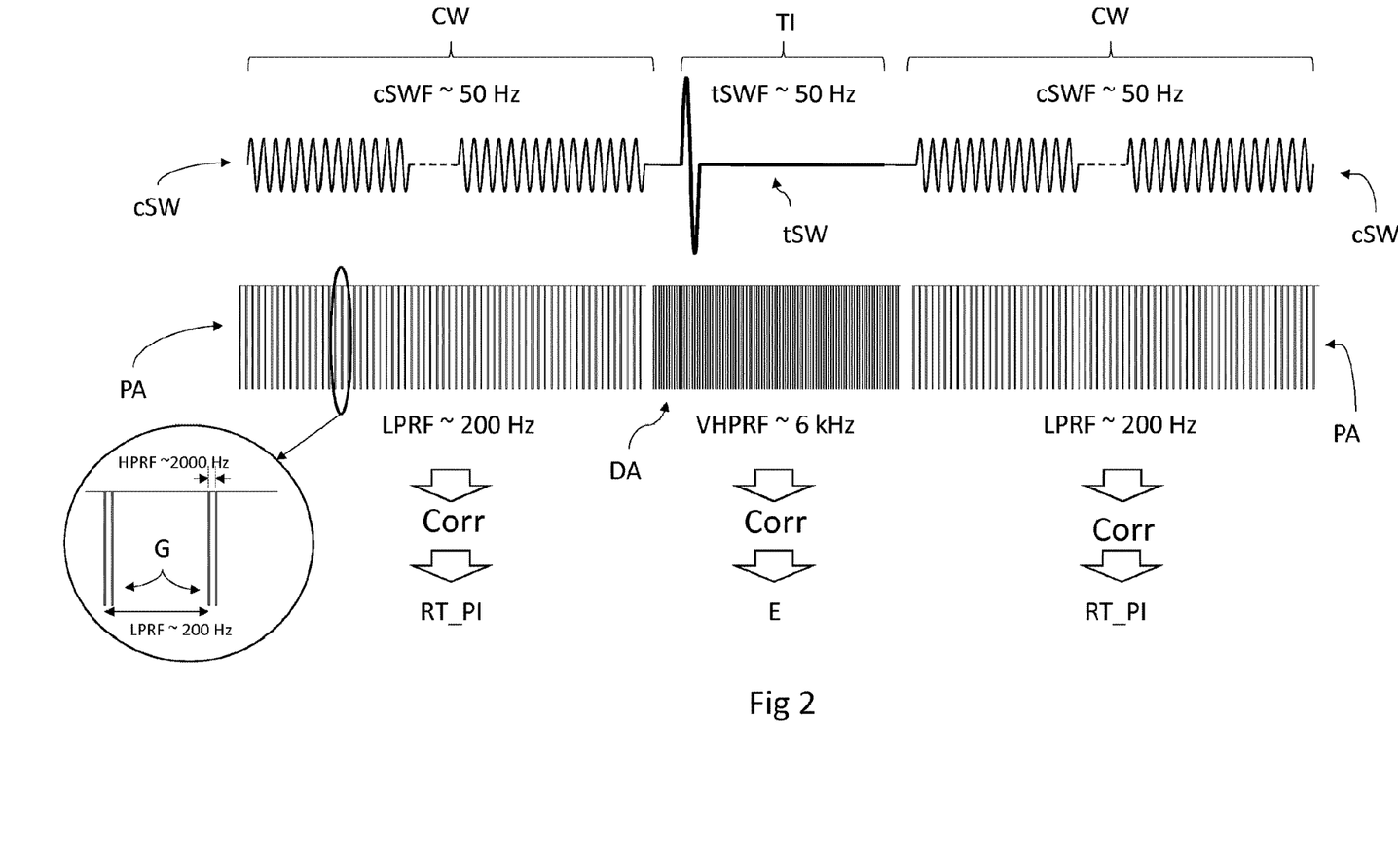
FIG. 2 schematically shows the vibrations applied by the vibrator and the ultrasonic acquisitions during the implementation of the method according to the invention illustrated in FIG. 1.

FIG. 2 schematically shows:
The continuous low frequency vibration cSW applied by the first vibrator during the step CW illustrated in FIG. 1;
The low frequency pulse tSW applied by the second vibrator during the step TI illustrated in FIG. 1;
The first series of ultrasonic acquisitions PA formed by groups G of acquisitions and generated by the ultrasonic transducer during the step CW illustrated in FIG. 1;
The second series of ultrasonic acquisitions DA generated by the ultrasonic transducer during the step TI illustrated in FIG. 1.

During the step of application of a continuous vibration CW, the vibrator oscillates at a frequency comprised between 5 and 500 Hz, with an amplitude comprised between 10 μm and 5 mm.

Advantageously, thanks to the low amplitude and to the low frequency of the continuous vibration an operator can easily maintain the probe in contact with the viscoelastic medium.

According to one embodiment, the same vibrator may be used to apply the continuous low frequency vibration cSWF and the low frequency pulse tSWF.

At the same time as the application of the continuous low frequency vibration, the ultrasonic transducer emits a first series of ultrasonic acquisitions PA formed by groups G of ultrasonic acquisitions. In the example illustrated in FIG. 2, each group G includes two ultrasonic acquisitions.

The groups G of ultrasonic acquisitions are emitted with a first repetition rate LPRF comprised between 10 Hz and 500 Hz. The ultrasonic acquisitions belonging to a same group G are emitted with an intra-group repetition rate HPRF comprised between 500 Hz and 10 kHz.

The ultrasonic transducer also detects the ultrasonic signals reflected during the generation of the ultrasonic acquisitions PA, as explained with reference to the step CW illustrated in FIG. 1. From the first series of ultrasonic acquisitions PA, it is possible to compute, by a step of correlation Corr between ultrasonic signals belonging to the same group G, the displacements generated in the viscoelastic medium by the propagation of the elastic wave generated by the continuous vibration applied by the vibrator.

Advantageously, by applying a correlation technique to the ultrasonic acquisitions belonging to a same group G—and thus brought closer in time—it is possible to detect small displacements and of the order of 1 μm to 10 μm.

As explained with reference to the step CW_P illustrated in FIG. 1, the displacements of the viscoelastic medium are next used to compute properties of the elastic wave such as variations in its amplitude and its phase as a function of depth in the medium. By comparing the measured properties with a theoretical model it is possible to deduce in real time a positioning indicator RT_IP.

For example, the positioning indicator may be linked to the linearity of the phase of the elastic wave as a function of depth in the medium to characterise. The indicator then depends on the quality of the adjustment of the evolution of the phase as a function of depth by a straight line.

For example, the positioning indicator may be linked to the decrease in the amplitude of the elastic wave as a function of depth in the medium to characterise. The indicator then depends on the quality of the fit in $1/Z^n$ where Z is the depth and n an integer coefficient comprised between 1 and 3.

For example, the value of the real time positioning indicator RT_IP is comprised between 0 and 1, with values close to 1 if the probe is correctly positioned with respect to the viscoelastic medium of interest.

If the value of the real time positioning indicator RT_IP is considered satisfactory, for example greater than a predetermined threshold, a step of application of a low frequency pulse TI is triggered.

The central frequency of the low frequency pulse tSFW is comprised between 10 Hz and 1000 Hz. The duration of the low frequency pulse is comprised between 1/(2*tSFW) and 1/tSFW.

The amplitude of the low frequency pulse is comprised between 100 μm and 10 mm.

According to one embodiment, the amplitude of the low frequency pulse may be modified on the basis of the properties of the elastic wave measured at the step CW_P.

The amplitude of the displacements caused by the propagation of the elastic wave is measured in the zone of interest. For example HAM the average amplitude measured in the zone of interest and HAR the reference average amplitude in the zone of interest are considered. Knowing that the displacements caused by the propagation of the pulse shear wave may be more difficult to measure, it is possible to calculate a multiplying coefficient b to apply to the set point of the low frequency pulse so that the amplitude of the displacements generated is optimal.

The amplitude AT of the set point of the low frequency pulse is computed as a function of ATR, the reference amplitude of the set point, and the coefficient b according to the equations:

$$b = \frac{HA_R}{HA_M}$$

And $$AT = b \times AT_R$$

The set point a(t) of the low frequency pulse is then defined in the following manner for a pulse duration of a period:

$$\begin{cases} a(t) = AT \times \sin(2\pi f t), & \text{if } t < 1/f \\ a(t) = 0, & \text{if } t \geq 1/f \end{cases}$$

Where f is the central frequency of the low frequency pulse also noted tSWF and t is time.

According to one embodiment, several low frequency pulses may be generated successively as described in the patent application FR 1351405.

As described with reference to the step TI of the method P according to the invention illustrated in FIG. 1, at the same time as the application of the low frequency pulse and the propagation of the transient shear wave, a second series of ultrasonic acquisitions DA is emitted with a second repetition rate VHPRF.

The second repetition rate VHPRF is comprised between 500 Hz and 100 kHz. The central frequency of each ultrasonic shot is comprised between 1 MHz and 15 MHz.

The ultrasonic transducer also detects the reflected ultrasonic signals and derived from the second series of ultrasonic acquisitions DA, as explained with reference to the step TI illustrated in FIG. 1. From the second series of ultrasonic acquisitions, it is possible to compute by a step of correlation Corr the displacements of the viscoelastic medium. Said displacements of the viscoelastic medium are generated by the propagation of the transient shear wave generated by the low frequency pulse applied by the vibrator. As explained with reference to the step TI_P illustrated in FIG. 1, the displacements of the viscoelastic medium are next used to compute the properties of the transient shear wave. In particular, it is possible to compute the propagation velocity $V_s$ of the shear wave and thus the elasticity E of the viscoelastic medium of interest. It is also possible to compute the Young's modulus and/or the shear modulus of the medium.

As illustrated in FIG. 2, after having obtained a measurement of the elasticity E of the viscoelastic medium, it is possible to repeat the method, by re-beginning with the step of application of a continuous vibration CW, followed by a step of application of a low frequency pulse (not illustrated in FIG. 2).

Figure 3:
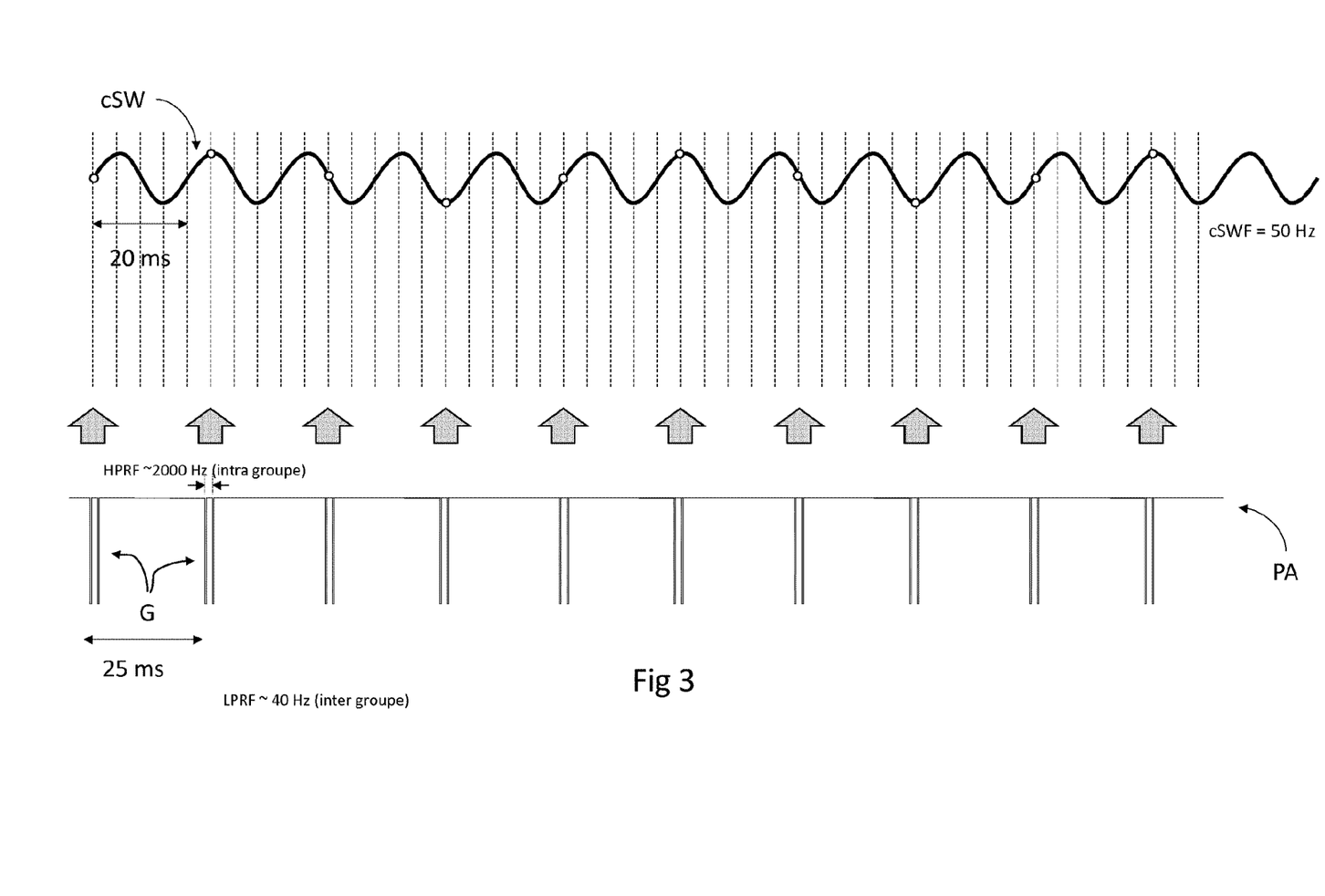
FIG. 3 schematically shows a particular embodiment of the elastography method illustrated in FIG. 1.

FIG. 3 shows a particular embodiment of the steps CW and CW_P of the method P according to the invention, called stroboscopic mode.

The continuous sinusoidal line schematically represents the continuous vibration cSW applied by the first vibrator. The continuous vibration cSW has for example a central frequency cSWF of 50 Hz corresponding to a period of 20 ms.

The continuous vertical lines represent the groups G of ultrasonic acquisitions forming the first series of ultrasonic acquisitions PA. The groups G are emitted with a first repetition rate LPRF. According to the stroboscopic acquisition mode, the first repetition rate LPRF is smaller than the central frequency of the continuous vibration cSWF.

The intra-group repetition rate is comprised between 500 Hz and 100 kHz, which makes it possible to measure small displacements of the order of 1 μm to 10 μm.

The white circles and the arrows along the continuous vibration cSW correspond to the sampling carried out by each group G of ultrasonic acquisitions.

Thanks to the fact that the repetition rate LPRF of the groups G is below the central frequency of the continuous vibration cSW, it is possible to sample in a complete manner the continuous vibration cSW at the end of several oscillation periods, as is illustrated by the white circles.

Advantageously, the stroboscopic mode makes it possible to sample in a complete manner the continuous vibration cSW while using a first low repetition rate LPRF. The use of a low repetition rate makes it possible to process the reflected signals in real time and thus to obtain the positioning indicator RT_IP in real time.

According to one embodiment, the first repetition rate LPRF is greater than the central frequency of the continuous vibration cSWF. This makes it possible for example to acquire two points per vibration period. A finer sampling is thus obtained with as many vibration periods or an equal sampling with fewer oscillation periods.

Figure 4:
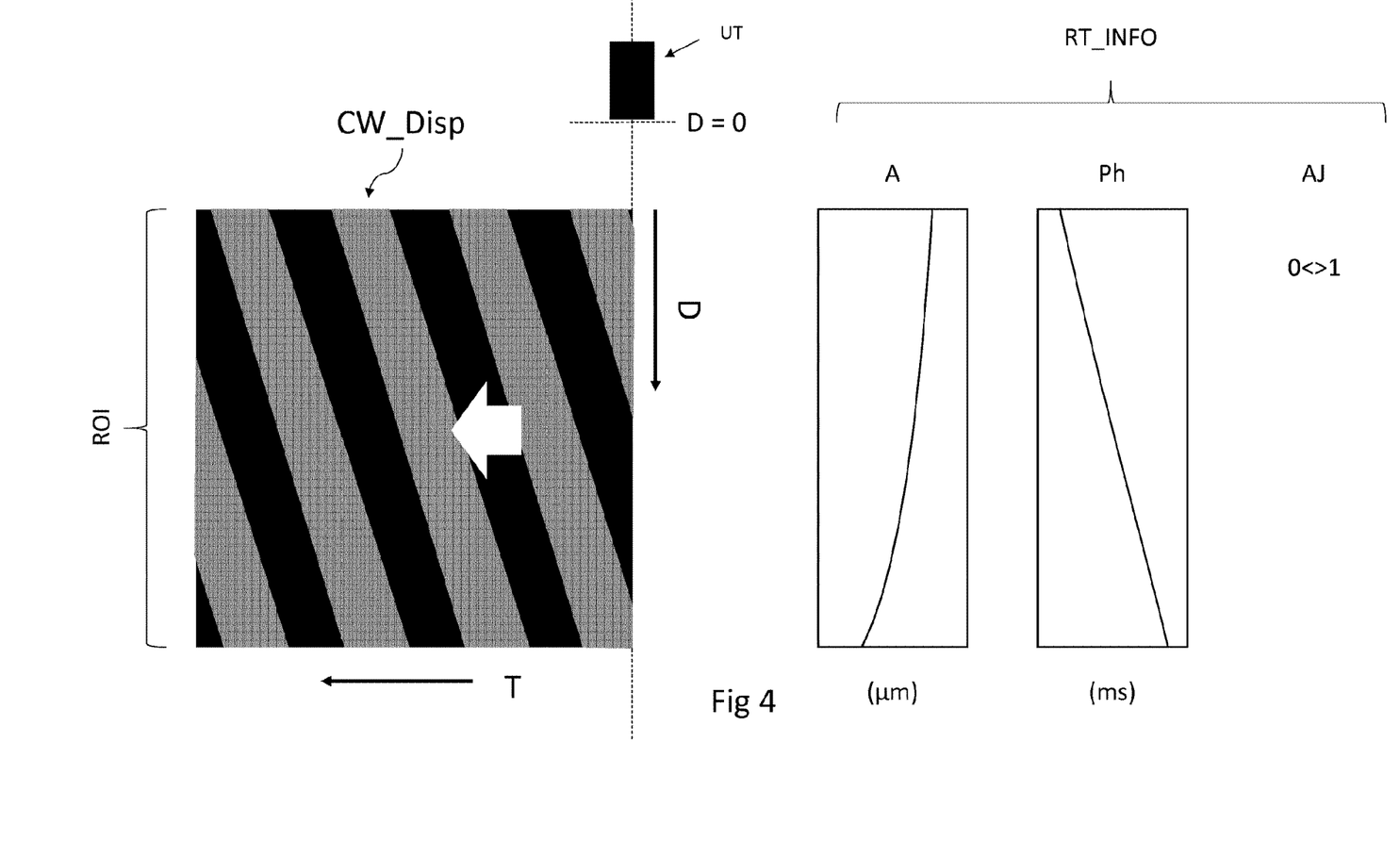
FIG. 4 shows the results obtained by implementing the part of the method according to the invention relative to the positioning of the vibrator.

FIG. 4 schematically shows the results obtained by implementing the part of the method P according to the invention relative to the positioning of the vibrator.

The graph CW_DISP shows the displacement (or any other movement parameter such as the velocity, the deformation, the deformation rate) of the viscoelastic medium in a region of interest ROI as a function of depth Z in the medium and of time T. The displacements are represented using a false colour scale, the lighter colours representing a displacement along the positive direction of the axis D. The displacements are caused by the continuous low frequency vibration applied by the vibrator and are measured by the ultrasonic transducer UT placed in contact with the surface of the medium, in Z=0.

From the displacements measured CW_DISP in the region of interest ROI within the viscoelastic medium, it is possible to extract in real time information RT_INFO concerning the elastic wave propagating within the medium and generated by the continuous vibration. Examples of such properties are the amplitude A and the phase Ph of the elastic wave as a function of depth within the medium.

By comparing the values of A and Ph measured with predetermined thresholds it is possible to determine a positioning indicator of the vibrator with respect to the viscoelastic medium. If the value of the positioning indicator is higher than a predetermined threshold, the measurement of elasticity of the medium by transient elastography is considered valid.

Alternatively, it is possible to obtain an adjustment quality parameter AJ between the measured quantities A and Ph and a theoretical model describing the amplitude and phase of an elastic wave propagating within the medium. In this case, the positioning indicator is obtained from the adjustment quality parameter AJ. For example, an adjustment quality parameter is the determination coefficient $R^2$ giving the quality of the prediction of the linear regression of the curve of the phase lag as a function of depth in the studied depth range.

According to one embodiment, the adjustment quality parameter AJ is comprised between 0 and 1.

Once calculated, the positioning indicator may be displayed in the form of a number or a letter or by using a colour scale. Alternatively, the positioning indicator may be a simple visual indication of "Positioning OK" type indicating that the operator can trigger the transient elastography step.

Figure 5:
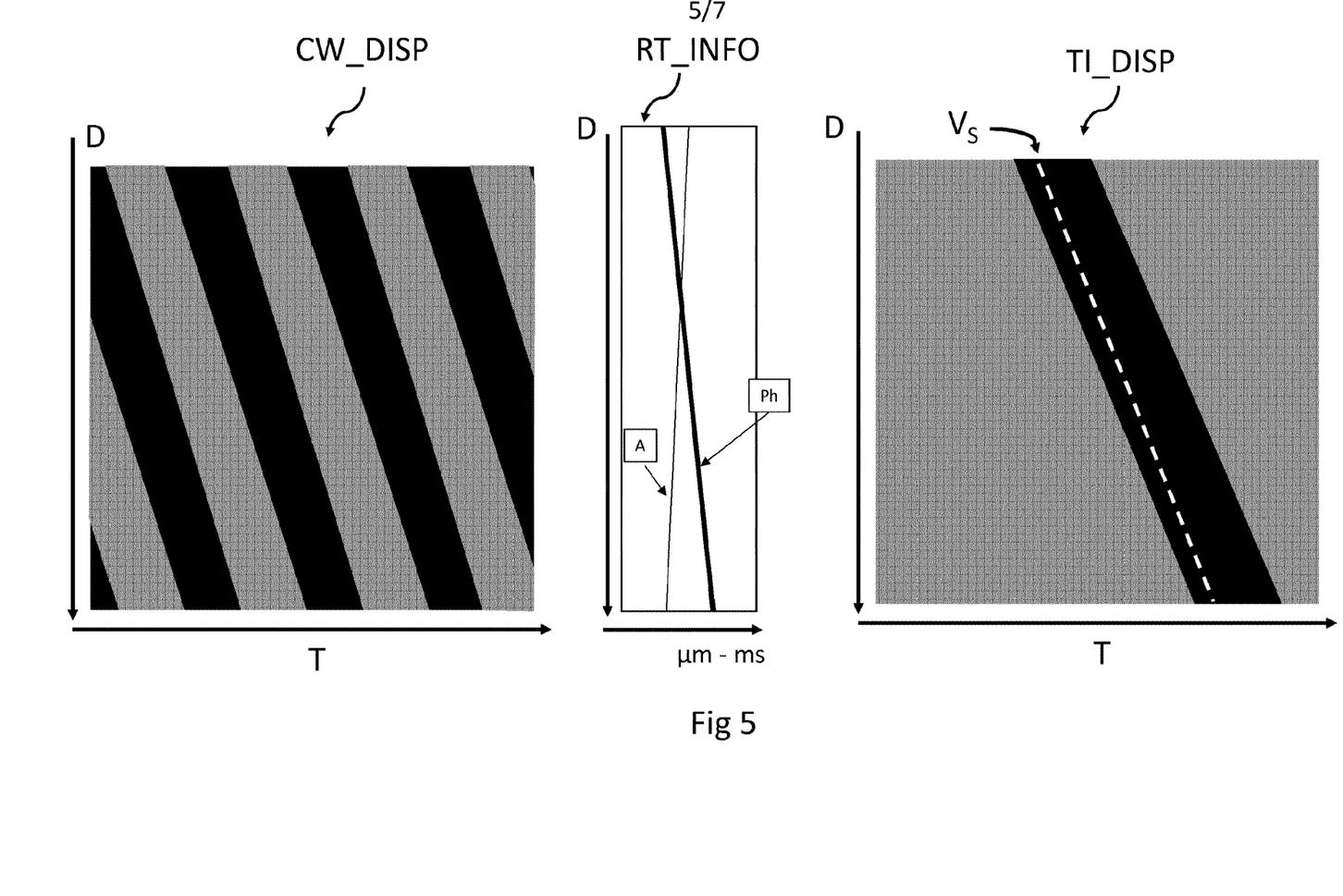
FIG. 5 shows the results of the implementation of the method illustrated in FIG. 1.

FIG. 5 shows the results obtained by implementing the method P according to the invention.

The graph CW_DISP represents the displacements measured in the presence of an elastic wave in the medium, as has been described with reference to FIG. 4.

The graph RT_INFO represents the amplitude A and phase Ph of the stationary wave measured in real time as explained with reference to FIG. 4. From the graph RT_INFO, a positioning indicator may be computed and displayed in real time.

The graph TI_DISP represents the measured displacements following the application of a low frequency pulse as a function of depth D in the medium and of time T. In other words, the graph TI_DISP represents a pulse elastogram. The displacements are represented using a false colour scale and correspond to the propagation of a transient shear wave within the viscoelastic medium.

From the displacements TI_DISP, it is possible to compute the propagation velocity $V_s$ of the transient shear wave and to work back to the elasticity of the medium.

As explained with reference to FIGS. 1, 2 and 3, during the implementation of the method P according to the invention, the graphs CW_DISP, RT_INFO and the positioning indicator of the vibrator are computed and displayed concomitantly.

Advantageously, thanks to the structure of the first series of ultrasonic acquisitions, the positioning indicator RT_IP as well as the graph RT_INFO may be computed and displayed in real time.

Conversely, the graph TI_DISP and the computation of the propagation velocity of the shear wave $V_s$ are only displayed if the position of the vibrator facing the viscoelastic medium is validated and if the step TI is triggered.

FIG. 5 may also be considered as a graphic representation of the results obtained during the implementation of the method P according to the invention and be displayed on a screen and consulted by the operator during the examination or the measurement.

Figure 6:
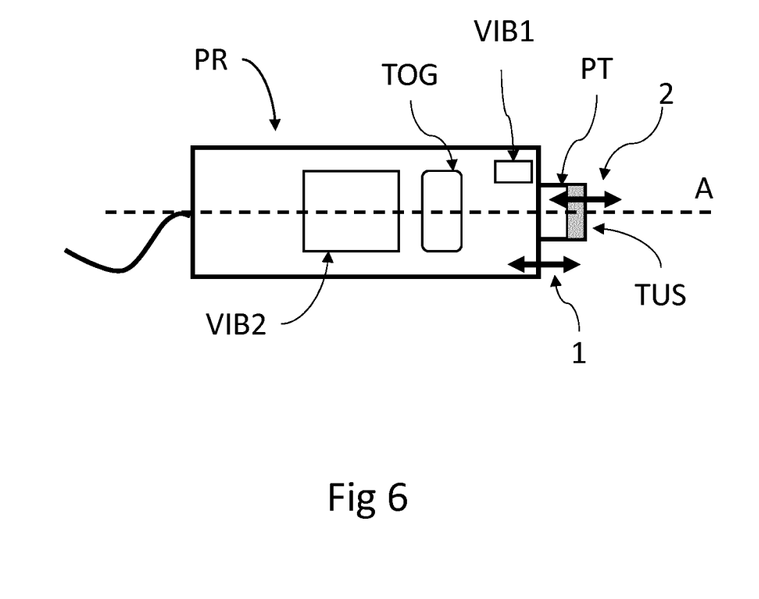
FIG. 6 represents a hybrid elastography probe according to the invention.

FIG. 6 schematically represents a hybrid elastography probe PR.

The probe PR includes:

A first vibrator VIB1 configured to apply to the viscoelastic medium a continuous low frequency vibration, the continuous low frequency vibration generating an elastic wave within the viscoelastic medium;

A second vibrator VIB2 configured to apply to the viscoelastic medium a low frequency pulse generating a transient shear wave within the viscoelastic medium;

An ultrasonic transducer TUS configured to emit:
a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition;
a second series of ultrasonic acquisitions, the ultrasonic acquisitions composing the second series being generated with a second repetition rate;

said probe being further configured to stop the application of the continuous vibration before the application of the low frequency pulse.

According to the embodiment illustrated in FIG. 6, the ultrasonic transducer TUS is mounted on the axis of the vibrator VIB2 applying the low frequency pulse.

According to one embodiment, the ultrasonic transducer TUS may be fixed to the body of the probe using a tip PT.

The first vibrator VIB1 makes the probe PR oscillate. During this oscillation, the ultrasonic transducer TUS is pushed against the viscoelastic medium applying the continuous low frequency vibration and creating the elastic wave within the medium.

According to one embodiment, the first vibrator VIB1 for the application of the continuous low frequency vibration includes a vibratory ring placed around the ultrasonic transducer TUS or around the probe tip PT.

The second vibrator VIB2 can apply the low frequency pulse to the viscoelastic medium according to several embodiments.

According to a first embodiment, the probe tip PT is moveable and may be actuated by the second vibrator VIB2. The ultrasonic transducer TUS is then pushed against the viscoelastic medium to apply the vibration, along the direction of the arrow 2 of FIG. 6.

According to a second embodiment, the probe PR is an inertial probe without moving parts. In this case, the movement of the second vibrator VIB2 within the probe PR leads to the movement of the probe and the continuous or pulsed vibration is once again applied by pushing the transducer TUS against the viscoelastic medium.

The axis of movement of the vibrator A is an axis of symmetry of the ultrasonic transducer TUS. For example, the ultrasonic transducer TUS may have a circular section, the axis A passing through the centre of the ultrasonic transducer TUS.

According to one embodiment, the probe PR includes control means TOG for triggering the application of a low frequency pulse, for example during the step TI of the method according to the invention.

Figure 7A:
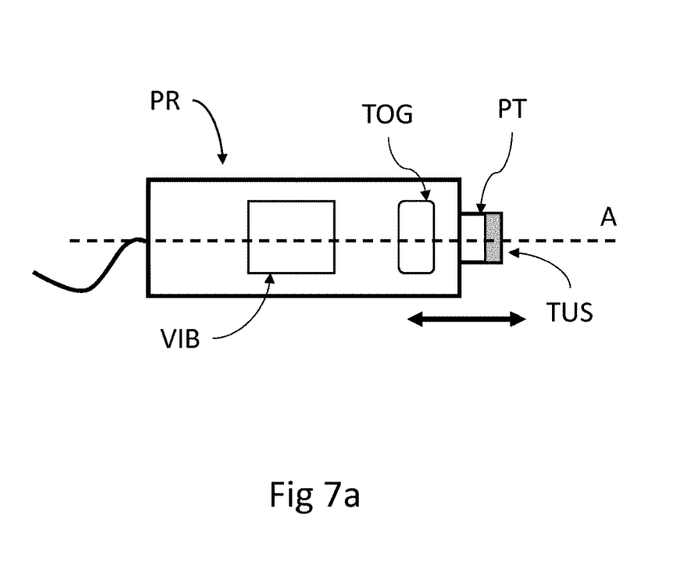
FIG. 7a represents a particular embodiment of the hybrid elastography probe according to the invention.

FIG. 7a schematically represents an embodiment of a probe PR for hybrid elastography according to the invention.

The probe PR includes:

A vibrator VIB for the application of a continuous or pulsed vibration to the viscoelastic medium of interest;

An ultrasonic transducer TUS for the emission of ultrasonic shots and the detection of the reflected ultrasonic signals.

The probe PR according to FIG. 7a thus includes a single vibrator intended to apply both the continuous low frequency vibration and the low frequency pulse.

According to one embodiment, the diameter of the ultrasonic transducer is comprised between 2 and 15 mm.

According to one embodiment the central frequency of the ultrasonic transducer is comprised between 1 MHz and 15 MHz.

According to one embodiment, the ultrasonic transducer TUS is a convex abdominal probe.

According to one embodiment of the probe PR, at least one of the vibrators is axisymmetric. In other words, at least one vibrator has an axis of symmetry.

According to one embodiment, the axis of symmetry of the axisymmetric vibrator corresponds to the axis of symmetry of the ultrasonic transducer TUS.

According to one embodiment, at least one of the vibrators of the probe has a ring shape and is arranged around the ultrasonic transducer TUS.

According to one embodiment, the probe further includes computing and display means for computing and displaying the real time positioning indicator RT_IP.

For example, the computing means include at least one microprocessor and one memory.

For example, the display means include a screen and/or a positioning indicator.

According to one embodiment, the probe includes a positioning indicator which is triggered when the probe is correctly positioned. This indicator may be a visual indicator, for example a change of colour of diodes. Alternatively, the indicator may be a sound or haptic indicator such as a change of type or amplitude of a vibration.

Figure 7B:
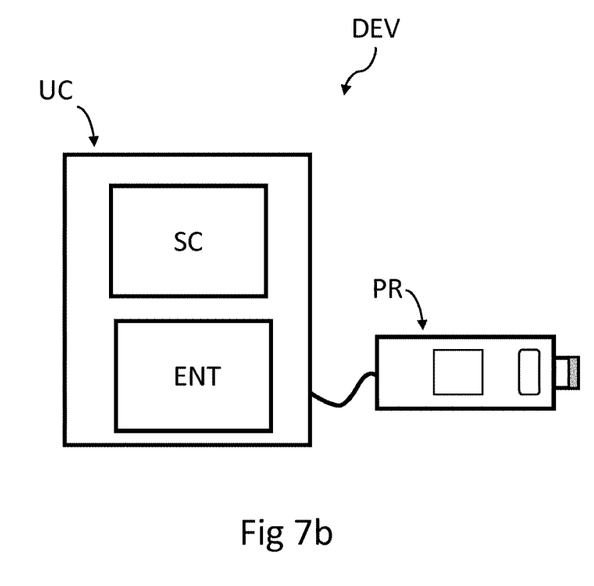
FIG. 7b represents a hybrid elastography device according to the invention.

FIG. 7b illustrates a hybrid elastography device according to the invention DEV. The device DEV according to the invention includes:

A probe PR according to the invention;
A central unit UC connected to the probe PR.
The central unit may comprise:
Computing means for processing the reflected ultrasonic signals;
A screen SC for displaying the results obtained at the different steps of the method P according to the invention;
Control or input means ENT for the control of the device by the operator.

The central unit UC may be connected to the probe PR by a wire link or by wireless communication means.

According to one embodiment the screen SC is suited for the display of the results illustrated in FIG. 5. The screen SC may also display in real time the position indicator RT_IP computed during the step CW_P of the method P according to the invention.

According to one embodiment, the central unit includes means configured to trigger automatically the application of a low frequency pulse on the basis of the value of the positioning indicator RT_IP computed and displayed in real time.

The invention claimed is:

1. A hybrid elastography method, comprising:
applying, using a first vibrator comprised in a probe in contact with a viscoelastic medium, a continuous low frequency vibration and generating, using an ultrasonic transducer in contact with the viscoelastic medium and concomitantly with the applying of the continuous low frequency vibration, a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition, the continuous low frequency vibration generating an elastic wave within the viscoelastic medium;
determining, from the first series of ultrasonic acquisitions, at least one property of the elastic wave within the viscoelastic medium, the property of the elastic wave within the viscoelastic medium being used to compute a real time positioning indicator of the probe with respect to the viscoelastic medium to study;
applying, using a second vibrator comprised in the probe in contact with the viscoelastic medium, a low frequency pulse and generating, using the ultrasonic transducer, a second series of ultrasonic acquisitions, the ultrasonic acquisitions composing the second series being generated with a second repetition rate, the low frequency pulse generating a transient shear wave propagating within the viscoelastic medium,
wherein the continuous low frequency vibration applied by the first vibrator is stopped before the application of the low frequency pulse by the second vibrator and the generation of the second series of ultrasonic acquisitions.

2. The hybrid elastography method according to claim 1, further comprising:
determining, from the second series of ultrasonic acquisitions, at least one property of the transient shear wave.

3. The hybrid elastography method according to claim 1, wherein the same vibrator is used to apply the continuous low frequency vibration and the low frequency pulse.

4. The hybrid elastography method according to claim 1, further comprising displaying in real time the real time positioning indicator.

5. The hybrid elastography method according to claim 1, wherein the applying of the low frequency pulse and the generating of the second series of ultrasonic acquisitions are only triggered if the positioning indicator satisfies a predetermined condition.

6. The hybrid elastography method according to claim 1, wherein the applying of the low frequency pulse and the generating of the second series of ultrasonic acquisitions are triggered automatically.

7. The hybrid elastography method according to claim 1, wherein the applying of the continuous low frequency vibration is only triggered if a contact force between the vibrator and the viscoelastic medium is above a predetermined lower threshold.

8. The hybrid elastography method according to claim 1, wherein the applying of the low frequency pulse is only triggered if a contact force between the vibrator and the viscoelastic medium is comprised between a predetermined lower threshold and a predetermined upper threshold.

9. The hybrid elastography method according to claim 1, wherein the first series of ultrasonic acquisitions is formed by a repetition of groups including at least two ultrasonic acquisitions having an intra-group repetition rate comprised between 500 Hz and 10 kHz and the first repetition rate comprised between 10 Hz and 10 kHz.

10. The hybrid elastography method according to claim 1, wherein the first repetition rate is lower than the continuous low vibration frequency.

11. The hybrid elastography method according to claim 1, wherein the first and second vibrators are different vibrators comprised in the probe.

12. A hybrid elastography method, comprising:
applying, using a first vibrator comprised in a probe in contact with a viscoelastic medium, a continuous low frequency vibration and generating, using an ultrasonic transducer in contact with the viscoelastic medium, a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition, the continuous low frequency vibration generating an elastic wave within the viscoelastic medium;

determining, from the first series of ultrasonic acquisitions, at least one property of the elastic wave within the viscoelastic medium, the property of the elastic wave within the viscoelastic medium being used to compute a real time positioning indicator of the probe with respect to the viscoelastic medium to study;

applying, using a second vibrator comprised in the probe in contact with the viscoelastic medium, a low frequency pulse and generating, using the ultrasonic transducer, a second series of ultrasonic acquisitions, the ultrasonic acquisitions composing the second series being generated with a second repetition rate, the low frequency pulse generating a transient shear wave propagating within the viscoelastic medium, wherein an amplitude of the low frequency pulse is determined on the basis of the properties of the elastic wave generated within the viscoelastic medium by the continuous low frequency vibration.

13. The hybrid elastography method according to claim 12, wherein the first vibrator and the second vibrator are the same such that a single vibrator is used to apply the continuous low frequency vibration and the low frequency pulse.

14. A hybrid elastography method, comprising:
applying, using a first vibrator comprised in a probe in contact with a viscoelastic medium, a continuous low frequency vibration and generating, using an ultrasonic transducer in contact with the viscoelastic medium, a first series of ultrasonic acquisitions, said first series of ultrasonic acquisitions including groups of ultrasonic acquisitions, the groups of ultrasonic acquisitions being generated with a first repetition rate, each group of ultrasonic acquisitions including at least one acquisition, the continuous low frequency vibration generating an elastic wave within the viscoelastic medium;

determining, from the first series of ultrasonic acquisitions, at least one property of the elastic wave within the viscoelastic medium, the property of the elastic wave within the viscoelastic medium being used to compute a real time positioning indicator of the probe with respect to the viscoelastic medium to study;

applying, using a second vibrator comprised in the probe in contact with the viscoelastic medium, a low frequency pulse and generating, using the ultrasonic transducer, a second series of ultrasonic acquisitions, the ultrasonic acquisitions composing the second series being generated with a second repetition rate, the low frequency pulse generating a transient shear wave propagating within the viscoelastic medium, wherein the continuous low frequency vibration applied by the first vibrator is stopped before the applying of the low frequency pulse by the second vibrator and the generating of the second series of ultrasonic acquisitions, and wherein the stopping of the continuous vibration of the vibrator and the application of the low frequency pulse are separated by a time interval greater than 10 ms.

15. The hybrid elastography method according to claim 14, wherein the first vibrator and the second vibrator are the same such that a single vibrator is used to apply the continuous low frequency vibration and the low frequency pulse.

16. A hybrid elastography probe comprising:
a first vibrator configured to apply to a viscoelastic medium a continuous low frequency vibration, the continuous low frequency vibration generating an elastic wave within the viscoelastic medium;
a second vibrator configured to apply to the viscoelastic medium a low frequency pulse generating a transient shear wave within the viscoelastic medium;
an ultrasonic transducer configured to emit:
a first series of ultrasonic acquisitions concomitantly with application of the continuous low frequency vibration by the first vibrator, said first series of ultrasonic acquisitions including groups of ultrasonic acquisitions, the groups of ultrasonic acquisitions being generated with a first repetition rate, each group of ultrasonic acquisitions including at least one acquisition;
a second series of ultrasonic acquisitions, the ultrasonic acquisitions composing the second series being generated with a second repetition rate;
said probe further being configured to stop the application of the continuous vibration before the application of the low frequency pulse.

17. The hybrid elastography probe according to claim 16, wherein at least one of the first and second vibrators has a same axis of symmetry as the ultrasonic transducer.

18. The hybrid elastography probe according to claim 16, wherein at least one of the first and second vibrators has a ring shape and is arranged around the ultrasonic transducer.

19. The hybrid elastography probe according to claim 16, further comprising means for computing and displaying the positioning indicator.

20. A hybrid elastography device comprising:
the hybrid elastography probe according to claim 19;
a central unit connected to the probe and including at least computing means for processing reflected ultrasonic signals, display means and control and/or input means.

21. The hybrid elastography probe according to claim 16, wherein the first vibrator and the second vibrator are the same such that a single vibrator is used to apply the continuous low frequency vibration and the low frequency pulse.

22. The hybrid elastography probe according to claim 16, wherein the first vibrator and the second vibrator are different vibrators.

* * * * *